(12) United States Patent
Lannutti

(10) Patent No.: US 6,598,663 B1
(45) Date of Patent: Jul. 29, 2003

(54) METHOD FOR DETECTING DENSITY GRADIENTS

(75) Inventor: John J. Lannutti, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/544,016

(22) Filed: Apr. 6, 2000

(51) Int. Cl.$^7$ .............................. B22C 1/02; G01N 21/88
(52) U.S. Cl. ................. 164/520; 164/150.1; 250/559.4; 356/237.1; 356/239.3
(58) Field of Search ................................ 264/21; 164/6, 164/517, 520, 138, 150.1, 154.1; 250/358.1, 559.4, 559.46; 356/237.1, 237.2, 240.1, 239.3

(56) References Cited

U.S. PATENT DOCUMENTS

| | | | | |
|---|---|---|---|---|
| 3,617,747 A | * | 11/1971 | Wilkinson et al. | 164/132 |
| 4,162,126 A | * | 7/1979 | Nakagawa et al. | 250/559.46 |
| 4,651,011 A | * | 3/1987 | Ors et al. | 250/458.1 |
| 4,802,195 A | * | 1/1989 | Wojcienchowski et al. | 378/204 |
| 5,242,007 A | * | 9/1993 | Remmers et al. | 164/132 |
| 6,102,009 A | * | 8/2000 | Nishiyama | 123/456 |
| 6,237,671 B1 | * | 5/2001 | Lassow et al. | 164/4.1 |
| 6,296,791 B1 | * | 10/2001 | Kobayashi et al. | 252/62.56 |

* cited by examiner

Primary Examiner—Jill L. Heitbrink
(74) Attorney, Agent, or Firm—Standley & Gilcrest LLP

(57) ABSTRACT

The present invention includes molding additives and molded materials. This invention also includes machines or electronic apparatus using these aspects of the invention. The present invention also includes methods and processes for making and using these devices and systems. In a preferred embodiment, a dye that fluoresces via ultraviolet absorption is dispersed in an organic additive. The additive is mixed with a molding material that is then formed into a shaped article by compaction. The resultant shaped article is then observed under an ultraviolet lamp to determine fluorescence variation, such variation corresponding to density gradients in the article.

16 Claims, 2 Drawing Sheets

METHOD FOR DETECTING DENSITY GRADIENTS

TECHNICAL FIELD OF THE INVENTION

The present invention is in the field of die molding and compaction.

BACKGROUND OF THE INVENTION

This invention relates to articles produced in a die molding process. More specifically, this invention relates to the determination of density gradients in molded components.

A variety of industries use compaction, as well as blow-molding, as a means of shaping material. This process is reasonably inexpensive and may be set up relatively easily. A problem exists with this procedure, however, in that density gradients are inevitable in all molding processes. These gradients can cause a host of processing problems downstream. These problems generally have an adverse effect on the cost of processing the molded parts. If the gradients are severe enough in a part, the least costly solution may be to reject or recycle the part, preferably prior to any thermal or other subsequent processing.

Unfortunately, density gradients are not detectable by the human eye. Expensive, sophisticated techniques are currently necessary to detect gradient variations in these parts, these techniques not being well. suited for a production environment.

It is therefore an object of the present invention to develop an inexpensive method of easily determining gradient variation of molded products in a production environment.

Although described with respect to the field of article molding and compaction, it will be appreciated that similar advantages of easy density visualization, as well as other advantages, may obtain in other applications of the present invention. Such advantages may become apparent to one of ordinary skill in the art in light of the present disclosure or through practice of the invention.

SUMMARY OF THE INVENTION

The present invention includes molding additives and molded materials. This invention also includes machines or electronic apparatus using these aspects of the invention. The present invention may also be used to upgrade, repair or retrofit existing machines or electronic devices or instruments of these types, using methods and components used in the art. The present invention also includes methods and processes for making and using these devices.

The present invention includes a method for detecting density gradients in molded articles of manufacture. The articles may be molded using any method known in the art, preferably compaction or blow molding. The method comprises, first, disbursing a fluorescence-capable dye in a molding additive, such as an organic-containing additive. It is preferred that the dye be capable of fluorescence due to infrared or ultraviolet absorption, most preferably due to ultraviolet absorption. The dye may be any appropriate such dye now known or subsequently discovered or developed.

The dye-containing additive is then disbursed or dissolved in a moldable material. If the moldable material is capable of properly dissolving or dispersing the dye alone, then the dye may be added directly to the moldable material and need not be added to a separate molding additive. The moldable material may be any appropriate material capable of being compacted or molded. The material is then molded into a shaped article.

The shaped article is then examined for fluorescence. The examination may be accomplished by any of several ways. A first method of examination involves directing a light source, preferably an ultraviolet or infrared light source, toward the shaped article. The light source should be capable of stimulating fluorescence in the fluorescence-capable dye. The shaped article is then visually inspected for variations in the resultant fluorescence of the article.

Another possible method of examination involves capturing at least one electronic image of the shaped article, the electronic image containing information regarding the fluorescence of the article. The electronic image is then analyzed. The image may be analyzed by any appropriate means, such as those involving quantitative determinations made by a computer or other processing device. These quantitative determinations preferably comprise density-fluorescence correlations.

Another method of examination involves passing a fluorescence detection device over the surface of the shaped article. The detection device is preferably connected to a feedback device, the feedback device adapted to signal when the fluorescence exceeds a threshold value. The signal may be any appropriate signal, such as a warning light, audible sound, or computer display. The fluorescence detection device may be moved over the article either manually or through the use of automation. Where automation is used, the automation apparatus may be adapted to remove from an assembly line or production process any articles wherein the fluorescence exceeds a predetermined threshold or where the variation in fluorescence exceeds a predetermined threshold.

An additional method of examination involves passing a microscope over the shaped article. The microscope may be any appropriate microscope adapted to detect fluorescence in a shaped article. The microscope may be a direct-view microscope or may utilize a camera connected to a computer or other display device. A user then views the shaped article using the microscope. The user may then make a determination as to whether the article passes inspection.

DETAILED DESCRIPTION OF THE PREFERRED EMBODIMENT(S)

Figure 1:
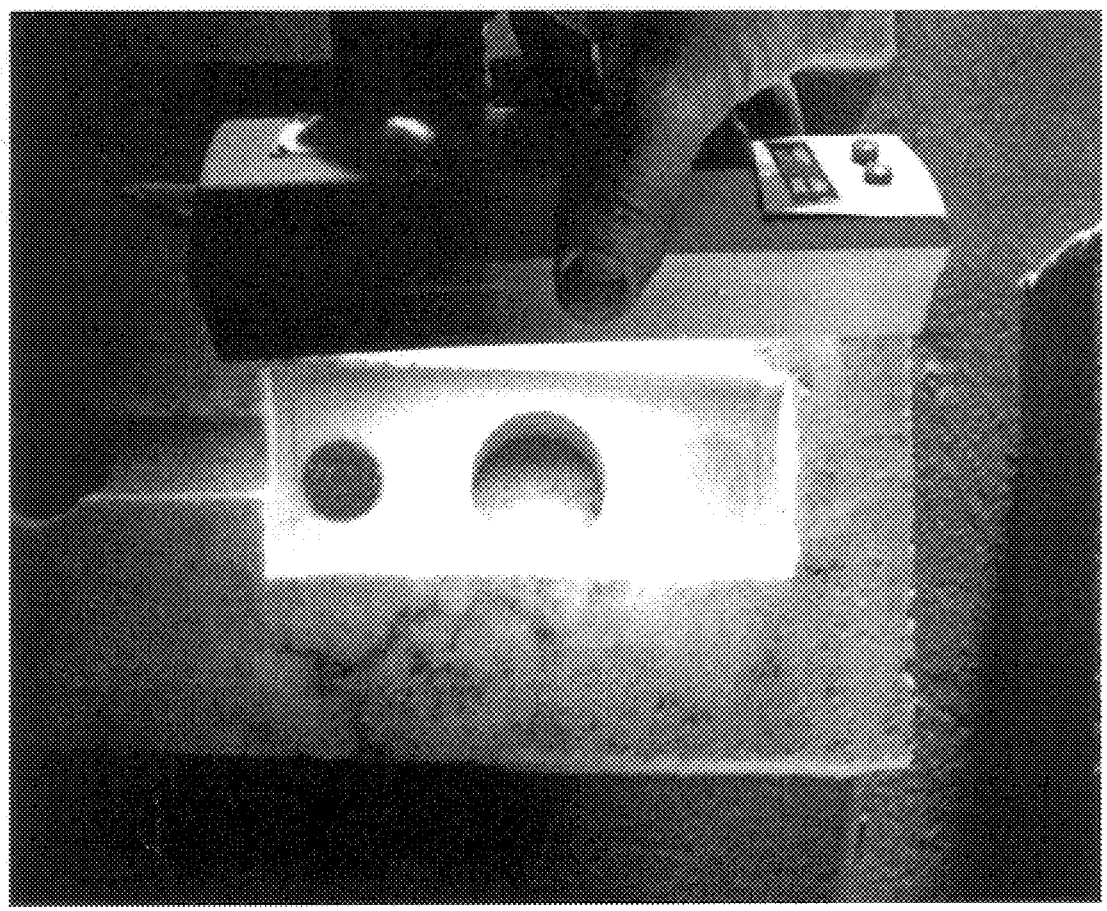
FIG. 1 is a pictorial view of a sand mold exhibiting varied fluorescence in accordance with one embodiment of the present invention.
Figure 2:
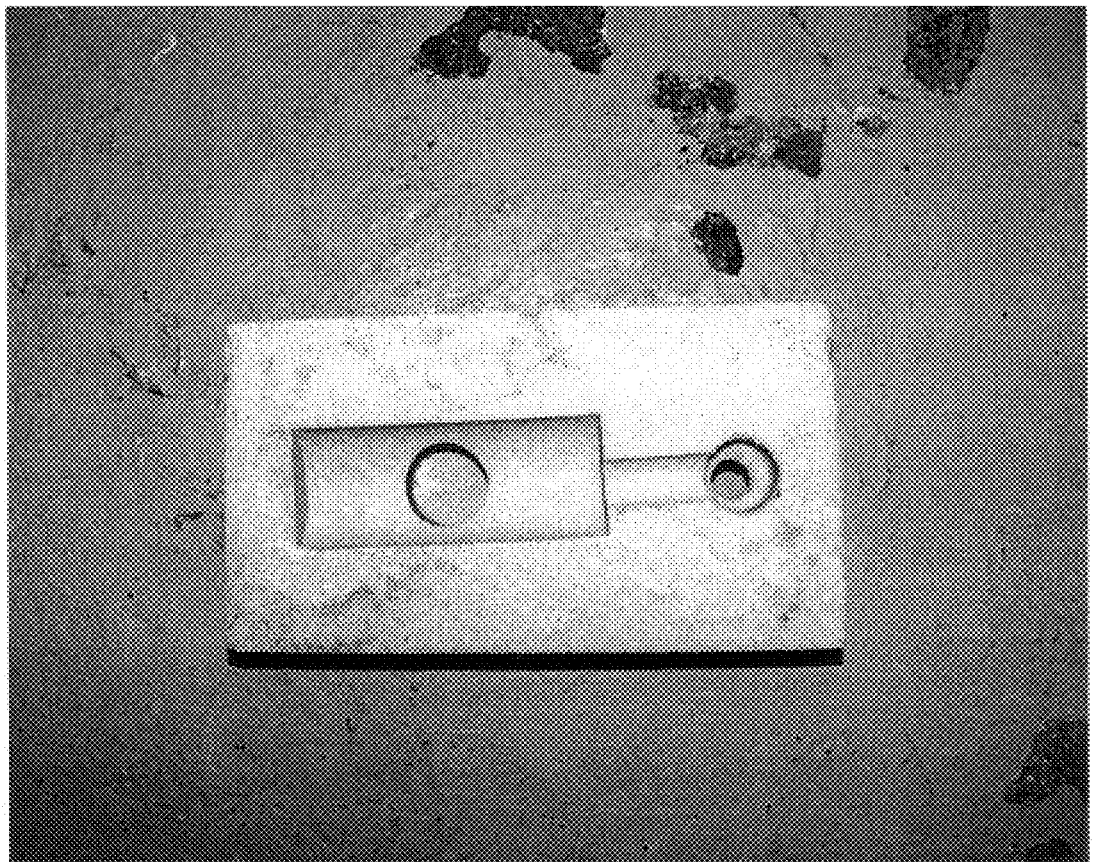
FIG. 2 is another pictorial view of a sand mold in accordance with one embodiment of the present invention.

In accordance with the foregoing summary, the following presents a detailed description of the preferred embodiment of the invention that is currently considered to be the best mode.

Organic additives are common to a broad range of compaction processes within several industries. If a gradient in the density of a product of one of these processes exists, then there must be not only an inorganic imbalance but also an organic imbalance. An indicator dye that is dissolved or dispersed in the organic phase may then serve as an effective means of visualizing the gradients as they intersect the exterior surface of the part.

A simple coloring agent will not be sufficient, however. Many compacted parts, especially in the foundry industry, are flat black in color. Therefore, a simple dye will not show any visible variation. Also, no manufacturer would favor the addition of significant quantities of relatively expensive colorants. This would not only increase component cost, but would also change thermal performance.

What is desired is a dye that fluoresces in only small quantities. A dye that fluoresces via ultraviolet absorption, such as Uvitex OB manufactured by Ciba-Geigy, may be readily available and appropriate for such a task. Infrared dyes may also be appropriate.

An experiment was conducted using a sample of Uvitex OB added to an organic foundry additive manufactured by Ashland Chemical. The dye was dissolved in one part of a two-part component system that cures at room temperature following mold formation. The remainder of the processing into a series of sand molds occurred in a normal fashion. No untoward effects of the presence of the dye on the mold formation process were observed.

As another test, both high and low density defects were deliberately introduced into the surface of these sand molds. The defects were visible when viewed using a 0.12 amp UV lamp. Despite the low lamp wattage, the higher-density areas glowed more brightly than the low-density areas. The lower density areas are plainly visible as dark patches in the surface of the mold.

The process may be used to inspect each compacted part produced, or may be used only when a process control problem is encountered. The inspection may be done in several different ways. In a first method, a simple visual inspection may be done. A technician may visually inspect a part using any one of a variety of ultraviolet sources, such as those manufactured by Spectroline or Blak-Ray. That person can then make a basic determination as to the quality of that part.

Another method may involve capturing at least one electronic image of a part, preferably after compaction but before any subsequent process such as heating or finishing. A computer or other processing device may then make a quantitative determination of density variation, such as by using image analysis linked to a database containing density-fluorescence correlations.

A third possible method may involve the use of an ultraviolet light pencil, like those manufactured by Spectroline, or any other appropriate, easily maneuverable hand-held UV detection device. The light pencil preferably contains an embedded fluorescence sensor that may be used to quickly examine problem areas. The light pencil may be connected to a computer or other device containing preset threshold information. The computer may then trigger a sensor, indicator, or other feedback device when the density goes outside a given range or exceeds a given threshold. Alternatively, the light pencil may be held and maneuvered by robotics over a given path and automatically analyzed by a computer or detector.

Another method may utilize an ultraviolet light emitting microscope, like that manufactured by Leica. The microscope may be adapted to analyze a part along the production line, or may be adapted to analyze a part pulled from the production line. The microscope may be used to examine small areas or small parts at high magnifications. The determination may then be made by a person viewing the magnified image, or may be made by a computer or detection device analyzing an electronic image signal derived from the microscope image.

The present invention may have a significant impact upon both domestic and international manufacturing. Several billion parts are manufactured by compaction each year. No technique for determining the extent of density gradients in these as-compacted components presently exists in any of these manufacturing facilities.

One example of how this technology can lead to increased manufacturing efficiency is provided by the foundry industry. In this market, sand molds costing only a few cents each are used to determine the quality of metallic products costing many thousands of dollars. Uncontrolled gradients can lead to extensive cleaning room time and days of unnecessary labor.

The use of indicator dyes could play a pivotal role as an indicator of 'bad' molds. This simple manufacturing aid is currently unavailable. Every sand mold is a "black box" whose performance cannot be predicted. Inspection capable molds would be of major value to almost every foundry that uses sand molds. Sixty percent of all metal castings in the United States are presently produced using sand molds. This constitutes $10.4 billion, or nearly 50 percent of the current total castings market.

The preferred embodiments herein disclosed are not intended to be exhaustive or to unnecessarily limit the scope of the invention. The preferred embodiments were chosen and described in order to explain the principles of the present invention so that others skilled in the art may practice the invention. Having shown and described preferred embodiments of the present invention, it will be within the ability of one of ordinary skill in the art to make alterations or modifications to the present invention, such as through the substitution of equivalent materials or structural arrangements, or through the use of equivalent process steps, so as to be able to practice the present invention without departing from its spirit as reflected in the appended claims, the text and teaching of which are hereby incorporated by reference herein. It is the intention, therefore, to limit the invention only as indicated by the scope of the claims and equivalents thereof.

What is claimed is:

1. A method for detecting density gradients in a sand mold, said method comprising the steps of:
    (a) disbursing a material additive in a formable sand material, said material additive comprising a fluorescence-capable dye;
    (b) molding said formable sand material into a sand mold;
    (c) examining the fluorescence of a region of said sand mold; and
    (d) determining the density gradient in said sand mold.

2. A method according to claim 1 wherein said fluorescence-capable dye comprises a dye capable of fluorescence due to infrared or ultraviolet absorption.

3. A method according to claim 1 wherein said material additive is an organic-containing additive.

4. A method according to claim 1 wherein said examining comprises:
    (a) directing a light source toward said sand mold, light from said light source capable of stimulating fluorescence in said fluorescence-capable dye; and
    (b) visually inspecting the resultant fluorescence of said region of said sand mold.

5. A method according to claim 4 wherein said light source is selected from the group consisting of ultraviolet and infrared light sources.

6. A method according to claim 1 wherein said examining comprises the steps of:
    (a) capturing at least one electronic image of said sand mold, said electronic image containing fluorescence information; and
    (b) analyzing said at least one electronic image.

7. A method according to claim 6 wherein said analyzing comprises quantitative determinations made by a computer or other processing device.

8. A method according to claim 7 wherein said quantitative determinations comprise density-fluorescence correlations.

9. A method according to claim 1 wherein said examining comprises passing a fluorescence detection device over the surface of said sand mold.

10. A method according to claim 9 wherein said fluorescence detection device comprises a UV light pencil.

11. A method according to claim 9 wherein said detection device is connected to a feedback device, said feedback device adapted to signal when said fluorescence exceeds a threshold value.

12. A method according to claim 11 wherein said signal is selected from the group consisting of warning lights, audible sounds, and visual displays.

13. A method according to claim 9 wherein additionally comprising automated apparatus adapted to move said fluorescence detection device over said surface.

14. A method according to claim 13 wherein said automated apparatus is adapted to remove said sand mold from the molding process when the fluorescence of a portion of said sand mold exceeds a threshold level.

15. A method according to claim 1 wherein said examining comprises:

(a) passing a microscope over said shaped article; and
(b) viewing said shaped article through said microscope.

16. A method according to claim 15 additionally comprising a remote display device in communication with said microscope.

* * * * *

UNITED STATES PATENT AND TRADEMARK OFFICE
CERTIFICATE OF CORRECTION

PATENT NO.     : 6,598,663 B1                                              Page 1 of 1
DATED          : July 29, 2003
INVENTOR(S)    : John J. Lannutti It is certified that error appears in the above-identified patent and that said Letters Patent is hereby corrected as shown below:

Column 6,
Lines 10 and 11, please delete the words "shaped article" and replace it with the words -- sand mold --.

Signed and Sealed this

Sixth Day of January, 2004

JAMES E. ROGAN
*Director of the United States Patent and Trademark Office*